(12) United States Patent
Chen et al.

(10) Patent No.: US 8,535,597 B2
(45) Date of Patent: Sep. 17, 2013

(54) BALLOON MOLD DESIGN

(75) Inventors: John J. Chen, Plymouth, MN (US); Calvin Fenn, Monticello, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 707 days.

(21) Appl. No.: 12/693,077

(22) Filed: Jan. 25, 2010

(65) Prior Publication Data

US 2010/0127436 A1 May 27, 2010

Related U.S. Application Data

(62) Division of application No. 11/367,553, filed on Mar. 3, 2006.

(51) Int. Cl.
*B29C 49/18* (2006.01)

(52) U.S. Cl.
USPC ............................................ 264/529; 264/530

(58) Field of Classification Search
None
See application file for complete search history.

(56) References Cited

U.S. PATENT DOCUMENTS

| | | | |
|---|---|---|---|
| 4,906,244 A | 3/1990 | Pinchuk et al. | |
| 4,963,313 A | 10/1990 | Noddin et al. | |
| 5,017,325 A * | 5/1991 | Jackowski et al. | 264/521 |
| 5,087,394 A | 2/1992 | Keith | |
| 5,255,889 A | 10/1993 | Collette et al. | |
| 5,328,468 A | 7/1994 | Kaneko et al. | |
| 5,334,146 A | 8/1994 | Ozasa | |
| 5,344,400 A | 9/1994 | Kaneko et al. | |
| 5,348,538 A | 9/1994 | Wang et al. | |
| 5,403,340 A | 4/1995 | Wang et al. | |
| 5,456,666 A | 10/1995 | Campbell | |
| 5,500,180 A | 3/1996 | Anderson et al. | |
| 5,525,388 A | 6/1996 | Wand et al. | |
| 5,556,383 A | 9/1996 | Wang et al. | |
| 5,587,125 A | 12/1996 | Roychowdhury | |
| 5,714,110 A | 2/1998 | Wang et al. | |
| 5,759,172 A | 6/1998 | Weber et al. | |
| 5,826,588 A | 10/1998 | Forman | |
| 5,833,657 A | 11/1998 | Reinhardt et al. | |
| 5,853,389 A | 12/1998 | Hijlkema | |
| 5,948,345 A | 9/1999 | Patel et al. | |
| 6,024,752 A | 2/2000 | Horn et al. | |
| 6,146,356 A | 11/2000 | Wang et al. | |
| 6,193,738 B1 | 2/2001 | Tomaschko et al. | |

(Continued)

FOREIGN PATENT DOCUMENTS

| | | |
|---|---|---|
| EP | 540858 | 5/1993 |
| JP | 60 189418 | 9/1985 |
| WO | 98/00318 | 1/1998 |

OTHER PUBLICATIONS

International Preliminary Report on Patentability dated Sep. 18, 2008 for PCT application corresponding o the present application.

*Primary Examiner* — Monica Huson
(74) *Attorney, Agent, or Firm* — Vidas, Arrett & Steinkraus, P.A.

(57) ABSTRACT

A catheter balloon molding system designed to facilitate multi-expansion step balloon forming processes using a segmented mold form. A multi-mating segment of the mold form, defining one end portion of the balloon, is retained throughout the multiple steps and the parison is kept in place in the multi-mating segment between expansion steps while the mold form is reconfigured for the next expansion step.

12 Claims, 9 Drawing Sheets

(56) References Cited

U.S. PATENT DOCUMENTS

| | | |
|---|---|---|
| 6,242,063 B1 | 6/2001 | Ferrera et al. |
| 6,270,522 B1 | 8/2001 | Simhambhatla et al. |
| 6,284,333 B1 | 9/2001 | Wang et al. |
| 6,287,506 B1 | 9/2001 | Hudgins et al. |
| 6,290,485 B1 | 9/2001 | Wang |
| 6,402,778 B2 | 6/2002 | Wang |
| 6,458,313 B2 | 10/2002 | Hudgins et al. |
| 6,561,788 B1 | 5/2003 | Gaudoin |
| 6,596,219 B2 | 7/2003 | Schaible et al. |
| 6,696,121 B2 | 2/2004 | Jung et al. |
| 6,712,833 B1 | 3/2004 | Lee et al. |
| 6,835,059 B2 | 12/2004 | Skinner et al. |
| 6,955,658 B2 | 10/2005 | Murray, II |
| 2002/0041059 A1 | 4/2002 | Jung, Jr. et al. |
| 2002/0125617 A1 | 9/2002 | Skinner et al. |
| 2005/0146085 A1 | 7/2005 | Holman et al. |
| 2005/0233025 A1 | 10/2005 | Zhang et al. |
| 2006/0033241 A1 | 2/2006 | Schewe et al. |

* cited by examiner

BALLOON MOLD DESIGN

CROSS-REFERENCE TO RELATED APPLICATIONS

This application is a Divisional application from Ser. No. 11/367,553, filed Mar. 3, 2006, the contents of which is hereby incorporated by reference.

FIELD OF THE INVENTION

This invention pertains to a mold apparatus for forming medical device parts such as balloons employed on catheters, endoscopes and the like.

BACKGROUND OF THE INVENTION

A typical method for forming medical device balloons includes molding the balloon from a hollow parison, for instance an extruded tubular parison. The mold form for such processes is adapted to receive the parison of thermoplastic material and has a cavity into or through which the parison extends. Heat is applied to the mold, for instance by immersion in a heated fluid, to soften the thermoplastic material. Concurrently, or in some sequence of heating and pressurization, the parison is pressurized to radially expand the softened thermoplastic material until it contacts and conforms to the shape of the cavity. This typical method may be practiced in a variety of known ways, for instance with or without an axial stretch step, which may be performed concurrent with or prior to radial expansion and at temperature above or below a glass transition temperature. A heat setting step or an annealing step may be performed after the balloon has been molded.

In mass production of medical device balloons, some processes produce substantial rejection rates. Parison shaping techniques, including multi-step balloon blowing processes going beyond simple axial stretching and radial expansion of straight tubes, are known. Examples of such techniques include U.S. Pat. No. 4,963,313, Noddin et al; U.S. Pat. No. 5,017,325, Jackowski et al; U.S. Pat. No. 5,334,146, Ozasa; U.S. Pat. No. 5,500,180, Anderson et al, U.S. Pat. No. 5,525,388, Wand et al; U.S. Pat. No. 5,714,110, Wang et al; U.S. Pat. No. 5,826,588, Forman; U.S. Pat. No. 5,948,345, Patel; U.S. Pat. No. 6,193,738, Tomaschko et al; and U.S. Pat. No. 6,458,313, Hudgins et al. At least some of these techniques, however, tend to increase balloon rejection rates when implemented in mass production.

When molding balloons utilizing certain polymer systems, for instance polyamide polymers such as nylon 12; polyester polymers such as polyethylene terephthalate, polyethylene naphthalate and polybutylene terephthalate; polyurethane polymers such as Pellethane® 2363-75D, multi-step blowing processes have been recommended. In such processes the parison is successively expanded in two or more radial expansion steps, each of which may be accompanied by a prior or concurrent axial stretching step.

In U.S. Pat. No. 5,348,538, Wang et al, there is described a tower molding apparatus for catheter balloons that immerses a parison/mold form in heated liquid media. A variant of this type of apparatus is also described in U.S. Pat. No. 5,714,110, Wang et al. In such apparatus parison tubing is threaded through a multi-part mold, the tubing is connected to an associated pressurized fluid source and the mold mounted in the apparatus in a largely manual process. Multi-step expansion has not previously been employed commercially in such an apparatus.

SUMMARY OF THE INVENTION

The present invention is directed to a novel mold design for preparing medical device balloons and to a balloon blowing process employing the mold design. The invention provides a catheter balloon molding system designed to facilitate multi-expansion step balloon forming processes, especially processes implemented using an immersion heating system. Balloons formed therewith may have improved quality and so lower rejection rate.

The invention utilizes a segmented mold system for forming a balloon from a tubular parison in a multi-step parison expansion process, the balloon having α- and β-end portions and an intermediate body portion therebetween, the system comprising:

a multi-mating end segment having a cavity sized to receive a portion of said parison and to define the α-end portion of the balloon configuration, said multi-mating end segment further having a mating edge portion adapted to mate with an adjacent mold portion, a first-expansion-step portion having a mating edge portion adapted to mate with said mating edge portion of the multi-mating end segment and having a cavity that receives a portion of the parison and defines a portion of a partially expanded configuration to which the parison will be expanded in a first radial expansion step, and a second-expansion-step portion having a mating edge portion adapted to mate with said mating edge portion of the multi-mating end segment and having a cavity that receives a partially expanded parison and defines a portion of the balloon configuration to which the partially expanded balloon parison will be further expanded in a second radial expansion step.

The first-expansion-step portion and second-expansion-step portion may themselves be composed of a single segment or two or more linearly sequential segments.

In at least one embodiment a second multi-mating end portion is provided to define the β-end of the balloon, with said first-expansion-step and second-expansion-portions defining a central region therebetween.

In other embodiments a single multi-mating α-end portion is utilized, with the first-expansion-step and second-expansion-step portions including the β-end portion of the mold cavity.

In some embodiments the second-expansion-step portion defines the final balloon configuration. In other embodiments further expansion-step portions may be employed to provide progressively larger or more complex body until the desired balloon configuration is reached.

In another aspect the invention is a method for forming a balloon using a mold system as described herein in a multi-step balloon forming process.

Still further aspects of the invention are described or are readily apparent from the accompanying drawings, detailed description and claims.

DETAILED DESCRIPTION OF PREFERRED EMBODIMENTS

Figure 1:
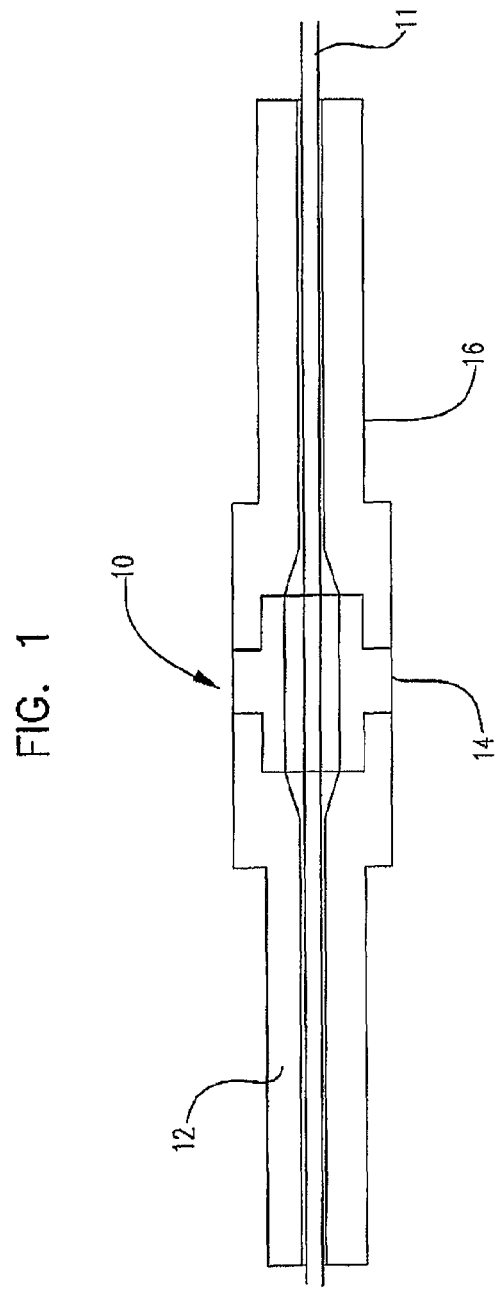
FIG. 1 is a side sectional view of a mold form for a first expansion step according to one embodiment of the invention, with a parison disposed therein.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The present invention provides a mold form and multiple expansion step balloon forming process that is particularly suited for use with a tower apparatus as described in U.S. Pat. No. 5,348,538 and U.S. Pat. No. 5,714,110.

The multi-part balloon molds described in U.S. Pat. No. 5,348,538 and U.S. Pat. No. 5,714,110 are comprised of three parts, proximal and distal end sections that define waist and cone portions of the balloon and a central portion that mates with the end portions at the large diameter of the respective cones and that defines the body region of the balloon.

In accordance with the present invention a multi-part balloon mold assembly is provided having an α-end and a β-end. The α-end of the mold may be configured to provide either the proximal end or the distal end of the balloon, but it is designed to be reused with the same parison in multiple successive mold assemblies. The mold assembly comprises at least an α-end segment and at least two body forms of different volume. The different body forms all mate with the same α-end segment so that the α-end segment is "multi-mating." The body forms are employed in an increasing volume sequence in a multi-expansion step balloon forming process without removal of said multi-mating α-end segment. Between expansion steps a portion of the mold form excluding the α-end form but including the body region is exchanged for a second-expansion-step portion comprising a larger volume body form while the parison remains mounted in the multi-mating α-end of the multi-mating α-end form so that proper parison orientation is retained and quality balloons are more reliably produced.

If the mold system is employed in a tower apparatus the exchange suitably is accomplished with the parison and α-end form held in place in the tower apparatus.

In some embodiments the mold form is a three part mold form that also includes a first β-end region segment. The enlarged body portion employed in the second expansion step may be configured to also mate with the first β-end segment so the first β-end segment is also multi-mating and may be reused in the second expansion step. Alternatively, the β-end segment may also be exchanged with a second β-end segment between expansion steps.

The balloon mold assembly may use three or more enlarged body portions if the parison is to be blown in three or more steps. Each such body portion mates with the multi-mating α-end segment so that the multi-mating α-end segment can be retained with the parison in the mold tower apparatus until the balloon formation steps have been completed.

In some embodiments the balloon mold form system if the invention comprises a segmented mold form that comprises a first β-end region form, a first-expansion-step portion comprising a first body portion and an enlarged second-expansion-step portion, the first-expansion-step portion and second-expansion-step portion being configured to form both the body portion of the balloon and the β-end of the balloon.

Referring to the Figures, FIG. 1 is a side sectional view of a mold form 10 assembled for first step expansion, with a parison 11 disposed therein. The mold form 10 is adapted to be heated by immersion in a heated fluid media. Mold form 10 comprises a multi-mating α-end segment 12, body segment 14, and β-end segment 16. In some embodiments the body segment diameter is sized at about 30% to about 90% of the final desired balloon diameter.

In the first expansion step of the invention the parison 11 is blown to conform to the mold form in a standard way, for instance using an immersion tower apparatus as described in U.S. Pat. No. 5,714,110.

Figure 2:
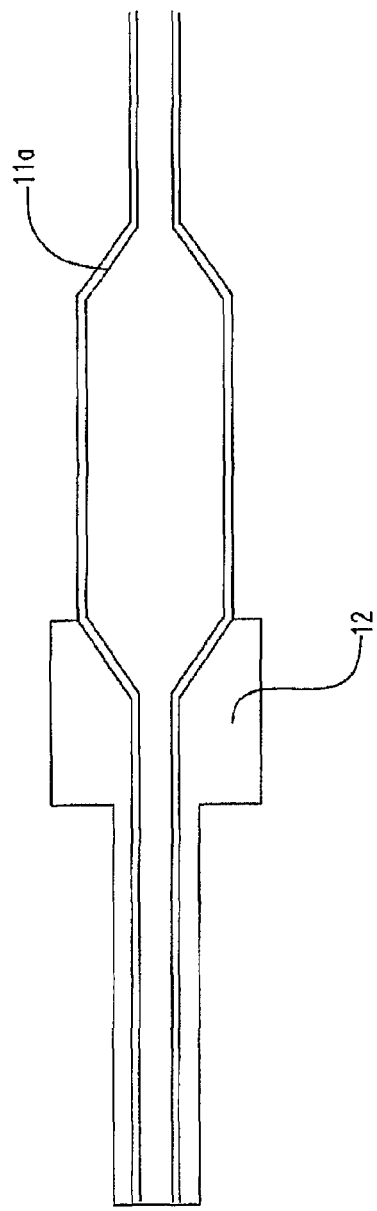
FIG. 2 is a view as in FIG. 1, after the first expansion step and removal of first body and β-end sections.

After the parison 11 has been blown in the first step the β-end segment 16 and the body segment 14 are removed, leaving the multi-mating α-end segment 12 and the partially blown parison 11a in place as shown in FIG. 2.

Figure 3:
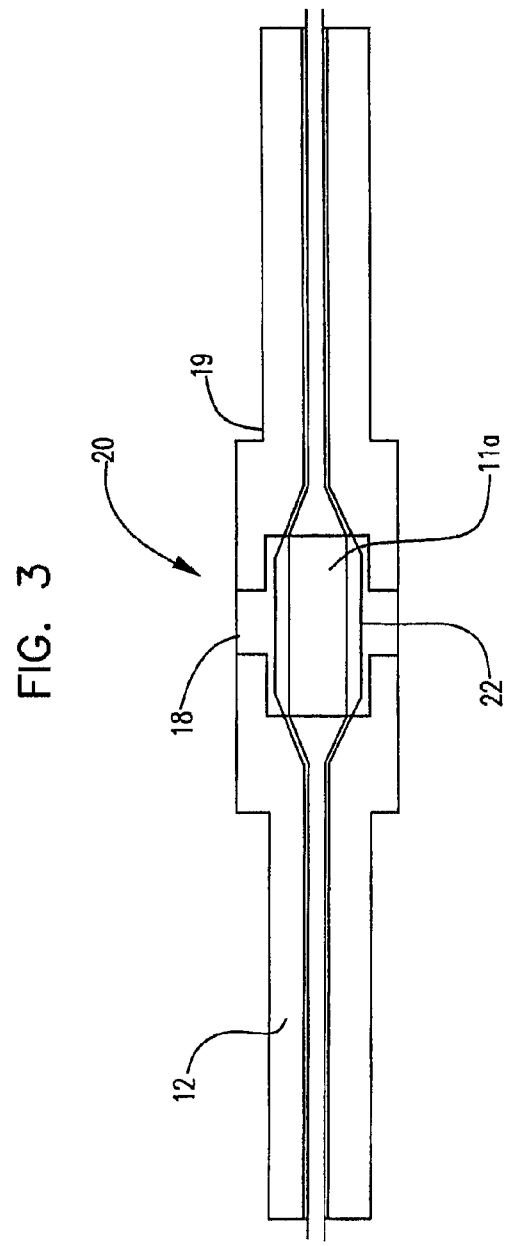
FIG. 3 is a side sectional view of a mold form for a second expansion step according to an embodiment of the invention, with a parison that has been partially blown in a first expansion step disposed therein.

The second-expansion-step portion comprising body segment 18 and a second β-end portion 19 are then slid in place over the parison 11a as depicted in FIG. 3, thus forming an enlarged mold form 20. While the α-end of the mold remains unchanged between mold forms 10 and 20, at least the body region 22 of the mold form 20 is enlarged relative to parison 11a.

In the second expansion step of the invention the parison 11a is blown to conform to the enlarged mold form 20, suitably in the same or similar way employed for the first expansion step to form the balloon. Optional annealing or heat setting steps may be performed before or after the formed balloon is removed from the mold.

In some embodiments more than two expansion steps may be needed, for instance for very large balloons intended for mounting on very small diameter catheters and for materials that are especially difficult to mold under the constraints of the particular molding apparatus and molding conditions. One or more further expansion-step portions may be exchanged in the same manner until the desired balloon configuration has been achieved.

Figure 4:
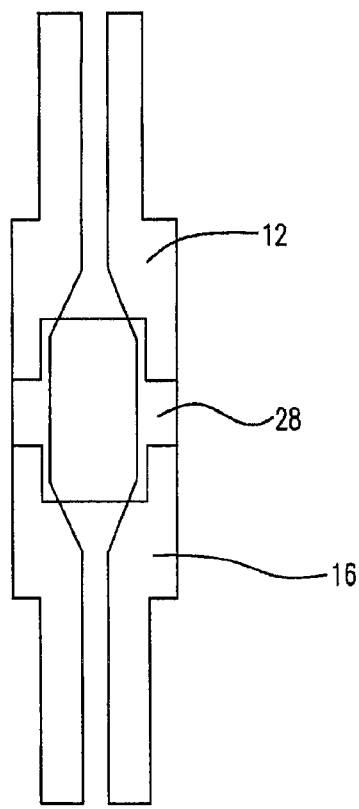
FIG. 4 is a side sectional view of an alternate embodiment of a mold form for a second step expansion.

FIG. 4 depicts an alternate embodiment of a mold form 26 for a second expansion step. The body segment 28 has been configured to mate with both the original α-end segment 12 and the original β-end segment 16.

Figure 5:
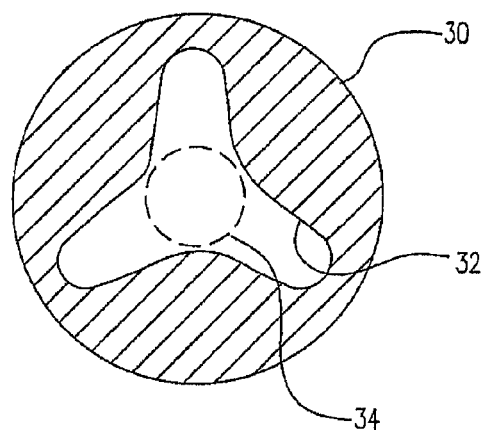
FIG. 5 is a cross sectional view of an alternate embodiment of a second body section of a mold form that may be utilized in the invention.

FIG. 5 is a cross-sectional view of an alternate embodiment of a second body segment 30 that may be utilized for the second expansion step of the invention. The body segment 30 has a lobed configuration for the mold cavity 32. The configuration of the partially blown parison from the first step expansion may be cylindrical as shown by the phantom line 34 or it may also be lobed in a similar but smaller configuration to that of cavity 32.

Figure 6:
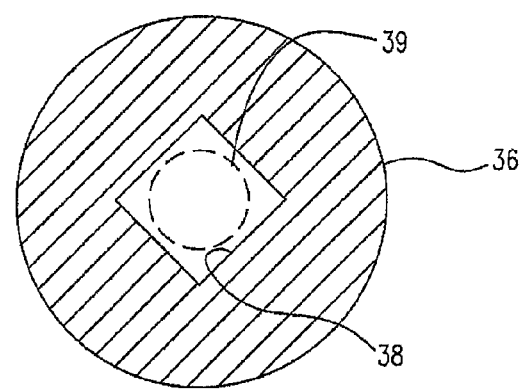
FIG. 6 is a cross sectional view of another alternate embodiment of a second body section that may be utilized for the second expansion step of the invention.

FIG. 6 is a cross-sectional view of another alternate embodiment of a second body segment 36 that may be utilized for the second expansion step of the invention. The body segment 36 has a square configuration for the mold cavity 38. The configuration of the partially blown parison from the first step expansion may be cylindrical as shown by the phantom line 39 or it may be a square that has shorter sides than that of cavity 38.

Figure 7:
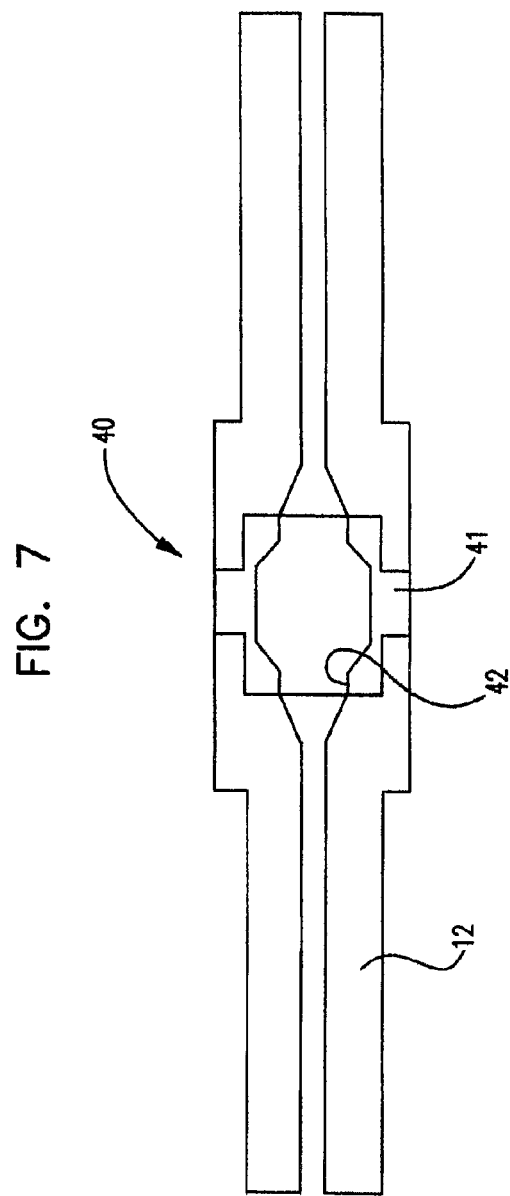
FIG. 7 is a side sectional view of a further alternate embodiment of a second body section.

FIG. 7 is a side-sectional view of an alternate embodiment of a mold form 40 for a second expansion step. The mold form includes a body segment 41 that may be utilized for a second expansion step of the invention. The body segment 41 has a stepped diameter configuration for the mold cavity 42. The configuration of the partially blown parison from the first step expansion may be cylindrical or it may also have a smaller diameter stepped diameter profile.

Other lobed, polygonal or stepped balloon configurations may be utilized. Without limitation other stepped diameter balloons as depicted in U.S. Pat. No. 6,402,778 may also be prepared using correspondingly configured forms for the second expansion stage body form.

Figure 8:
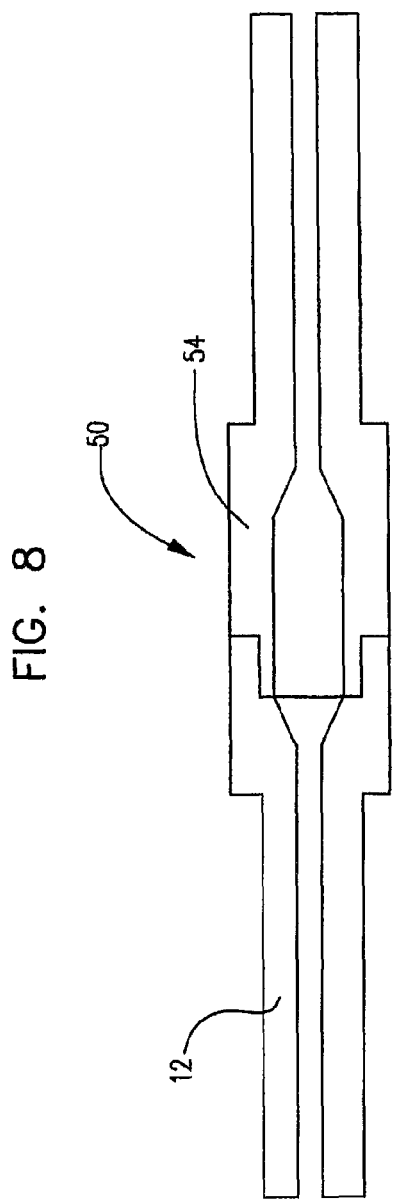
FIGS. 8 and 9 are side sectional views according to another embodiment of the invention of mold forms a first expansion step and a second expansion step, respectively.
Figure 9:
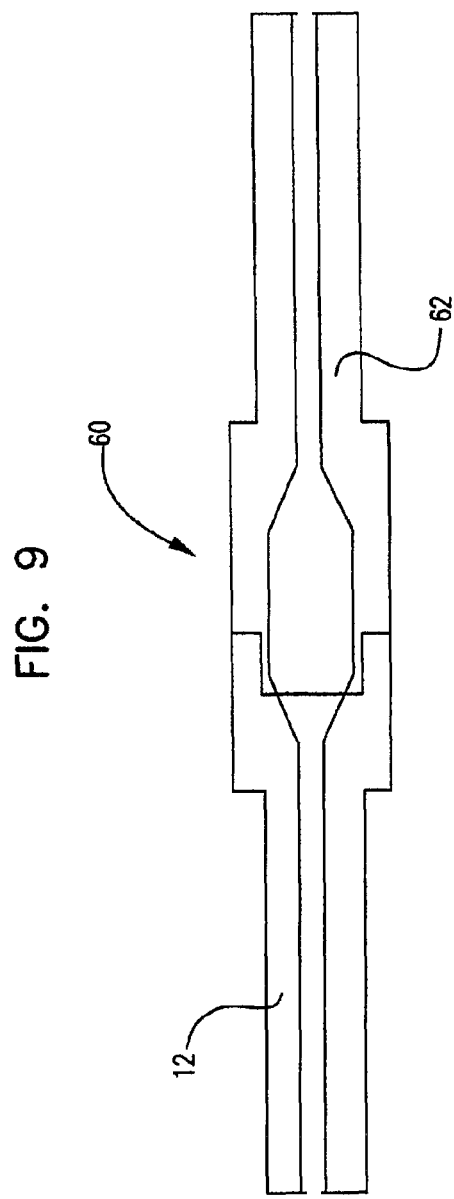

FIG. 8 shows a mold form 50 assembled for a first expansion step. Mold form 50 comprises a multi-mating α-end segment 12, and a second segment 54 that combines the body and β-end as a single piece. FIG. 9 shows a corresponding mold assembly 60 for a second expansion step comprising the same multi-mating α-end segment 12 of FIG. 8 mated with a larger second expansion portion 22.

Mold forms of the invention may be made of any suitable material, preferably one which provides for a highly polished or glassy cavity surface. Metal, such as titanium or stainless steel, are exemplary materials. Glass and ceramic materials may also be employed. Composite and laminate materials are also suitable. Preferred are materials which have high heat conductivity, especially metals such as stainless steel, titanium, aluminum and the like. In some cases various segments of the mold form may be made of different materials.

The mold forms of the invention may be adapted to provide variable body lengths, for instance by using variable length body segments as described in U.S. Pat. No. 6,835,059.

The tubular parison employed in the inventive method may be a straight tube, as extruded, or a tube that has been axially stretched before expansion. The tubular parison is not necessarily homogenous along its length. The parison may be multilayered, using the same or different materials in the various layers. It may also have a varying thickness, for instance resulting from parison processing such as the necking steps described in U.S. Pat. No. 4,963,313, Noddin, et al; U.S. Pat. No. 5,556,383, Wang, et al; or U.S. Pat. No. 5,087,394, Keith, or grinding steps such as described in U.S. Pat. No. 6,193,738, Tomaschko et al. The parison may be formed of longitudinal segments of different materials such as described in U.S. Pat. No. 6,024,752, Horn et al.

Following the expansion steps of the inventive method the balloons may be simply cooled; "heat set" at a still higher pressure and/or temperature than the expansion temperature and/or pressure; or "heat shrunk" at an above-ambient pressure and temperature, at least one of which is lower than the blow-forming temperature and pressure. See U.S. Pat. No. 5,403,340, Wang et al; EP 540858, Advanced Cardiovascular Systems, Inc.; and WO 98/03218, Scimed Life Systems.

The invention may be used in preparation of high strength medical balloons of any type. Particular advantages are in peripheral vascular applications where large differential between catheter diameter and balloon diameter is desirable. The inventive forms and techniques may be used to form balloons used in various gastrointestinal surgical procedures, for instance balloons described in WO 98/03218.

Suitably the balloons are formed by expansion of tubing at net a hoop ratio (mold diameter/tubing ID as extruded) of between 3 and 12, preferably between 4 and 10, although other ratios may be suitable for some applications.

Combinations of the techniques and systems described herein may also be employed.

Any balloon material suited to molding may be employed in the inventive method. Balloon materials which may be advantageously employed in the invention are well known. Any material which can be molded from a parison may be feasibly employed in the invention. Such materials include polyesters such as PET, PEN and PBT, polyurethane block copolymers such as ISOPLAST 301, PELLETHANE 2363-75D, and other materials described in U.S. Pat. No. 4,950,239 or U.S. Pat. No. 5,500,180; polyamide block copolymers such as PEBAX 6333, PEBAX 7033 and PEBAX 7233, and other materials described in U.S. Pat. No. 5,556,383; polyamides such as nylon 12, nylon 11, nylon 10, aromatic polyamides and other materials described in U.S. Pat. No. 4,906,244 and U.S. Pat. No. 5,328,468; polymer blend materials such as single or multiphase blends of liquid crystal polymers in another polymer, such as described in U.S. Pat. No. 6,242,063, U.S. Pat. No. 6,284,333 and U.S. Pat. No. 6,596,219; and polyester elastomer balloons such as ARNITEL EM 740, HYTREL 8238, and other materials described in U.S. Pat. No. 5,556,383, U.S. Pat. No. 6,146,356 and U.S. Pat. No. 6,270,522. Still other materials that may be employed include polyarylene sulfides as described in U.S. Pat. No. 5,344,400, Kaneko and polyetheretherketones as described in U.S. Pat. No. 5,833,657.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A multi-step balloon forming process comprising
providing a tubular parison of thermoplastic material
expanding the tubular parison in a first expansion step to provide a partially expanded parison and
expanding the partially expanded parison in a second expansion step, wherein
the first expansion step is performed in a segmented mold form comprising:
a multi-mating α-end segment having a cavity sized to receive a portion of said tubular parison and to define an α-end portion of the balloon, said multi-mating end segment further having a mating edge portion adapted to mate with an adjacent mold portion, and
a first-expansion-step portion having a mating edge portion adapted to mate with said mating edge portion of the multi-mating α-end segment and having a cavity that receives a portion of the parison and defines a portion of a partially expanded configuration to which the parison is expanded in the first expansion step, and the second expansion step is performed in a segmented mold form comprising:

said multi-mating α-end segment, and a second-expansion-step portion having a mating edge portion adapted to mate with said mating edge portion of the multi-mating α-end segment and having a cavity that receives the partially expanded parison and defines a portion of the balloon configuration to which the partially expanded parison is expanded in the second expansion step.

2. A method as in claim 1 wherein, between the first and second expansion steps the first-expansion-step portion is removed from the mold form and, during removal thereof, the partially expanded parison is held in engagement with the multi-mating α-end segment.

3. A method as in claim 2 wherein, prior to the second expansion step the second-expansion-step portion is assembled over the partially expanded parison and into mating relationship with the multi-mating α-end segment.

4. A method as in claim 2 wherein in the first expansion step the mold form further comprises a multi-mating β-end segment having a cavity sized to define the β-end portion of the balloon, said multi-mating β-end segment further having a mating edge portion adapted to mate with both said first-expansion-step portion and said second-expansion-step portion.

5. A method as in claim 4 wherein, prior to the second expansion step the second-expansion-step portion is assembled over the partially expanded parison and into mating relationship with the multi-mating α-end segment and the multi-mating β-end segment is assembled over the partially expanded parison and into mating relationship with the second-expansion-step portion.

6. A method as in claim 1 further comprising further expanding the parison in at least one further expansion step subsequent to said second expansion step.

7. A method as in claim 6 wherein each further expanding step in performed in a mold form that comprises said multi-mating α-end segment and a one further expansion-step-portion having a mating edge portion adapted to mate with said mating edge portion of the multi-mating α-end segment and having a cavity that defines a portion of the configuration to which the partially expanded parison is successively further expanded.

8. A method as in claim 1 wherein the α-end segment is sized to provide a distal end of the balloon when mounted on a catheter.

9. A method as in claim 1 wherein the α-end segment is sized to provide a proximal end of the balloon when mounted on a catheter.

10. A method as in claim 1 wherein at least one the first and second-expansion-step portions of the mold form consists of a single segment.

11. A method as in claim 1 wherein at least one of the first and second-expansion-step portions comprises two or more linearly sequential segments.

12. A method as in claim 1 wherein each of the first and second-expansion-step portions comprises two or more linearly sequential segments.

* * * * *